United States Patent
Cambronne (10) Patent No.: US 9,402,936 B2
(45) Date of Patent: Aug. 2, 2016

(54) MEDICAL DEVICES HAVING ALLOY COMPOSITIONS

(75) Inventor: Matthew Cambronne, Mounds View, MN (US)

(73) Assignee: Boston Scientific SciMed, Inc., Maple Grove, MN (US)

( * ) Notice: Subject to any disclaimer, the term of this patent is extended or adjusted under 35 U.S.C. 154(b) by 2022 days.

(21) Appl. No.: 11/780,060

(22) Filed: Jul. 19, 2007

(65) Prior Publication Data

US 2008/0071347 A1 Mar. 20, 2008

Related U.S. Application Data

(60) Provisional application No. 60/844,897, filed on Sep. 15, 2006.

(51) Int. Cl.
| | |
|---|---|
| *C22C 14/00* | (2006.01) |
| *C22C 16/00* | (2006.01) |
| *A61L 31/02* | (2006.01) |
| *C22F 1/18* | (2006.01) |
| *A61L 31/18* | (2006.01) |

(52) U.S. Cl.
CPC .............. *A61L 31/022* (2013.01); *A61L 31/18* (2013.01); *C22C 14/00* (2013.01); *C22C 16/00* (2013.01); *C22F 1/183* (2013.01); *C22F 1/186* (2013.01); *Y10T 428/12639* (2015.01)

(58) Field of Classification Search
CPC ........... A61F 2/91; C22C 14/00; C22C 1/005; C22F 1/183; C22F 1/186
See application file for complete search history.

(56) References Cited

U.S. PATENT DOCUMENTS

| | | | |
|---|---|---|---|
| 4,568,398 A * | 2/1986 | Wood et al. .................. 148/421 |
| 4,923,513 A | 5/1990 | Ducheyne et al. | |
| 4,958,625 A | 9/1990 | Bates et al. | |
| 5,090,419 A | 2/1992 | Palestrant | |
| 5,195,969 A | 3/1993 | Wang et al. | |
| 5,209,799 A | 5/1993 | Vigil | |
| 5,270,086 A | 12/1993 | Hamlin | |
| 5,336,234 A | 8/1994 | Vigil et al. | |
| 5,366,504 A | 11/1994 | Andersen et al. | |
| 5,368,045 A | 11/1994 | Clement et al. | |
| 5,674,242 A | 10/1997 | Phan et al. | |
| 5,780,807 A | 7/1998 | Saunders | |
| 6,146,404 A | 11/2000 | Kim et al. | |
| 6,171,327 B1 | 1/2001 | Daniel et al. | |

(Continued)

FOREIGN PATENT DOCUMENTS

JP  2000-254150  9/2000

OTHER PUBLICATIONS

ASM International, Materials Park, Ohio, vol. 3: Alloy Phase Diagrams, "Binary Alloy Phase Diagrams", pp. 2•38, 2•78, 2•150, 2•161, 2•180, 2•205, 2•290, 2•319 and 2•341, Dec. 1992.*

(Continued)

*Primary Examiner* — Jessee Roe
(74) *Attorney, Agent, or Firm* — Pauly, DeVries Smith & Deffner, L.L.C.

(57) ABSTRACT

A medical device includes an alloy having a microstructure that provides desirable properties. The alloy can be a eutectoid composition of e.g. titanium as a major constituent and any combination of iridium, platinum, chromium, gold, silver, bismuth, manganese, palladium, cobalt, copper, iron, and/or nickel as a minor constituent, wherein the alloy forms at least a portion of the medical device.

1 Claim, 6 Drawing Sheets

(56) References Cited

U.S. PATENT DOCUMENTS

| | | | |
|---|---|---|---|
| 6,287,331 | B1 | 9/2001 | Heath |
| 6,342,062 | B1 | 1/2002 | Suon et al. |
| 6,409,792 | B1 * | 6/2002 | Schutz et al. ............... 75/10.18 |
| 6,726,712 | B1 | 4/2004 | Raeder-Devens et al. |
| 7,087,077 | B1 * | 8/2006 | Van Dijk et al. ............. 623/1.15 |
| 2004/0044397 | A1 | 3/2004 | Stinson |

OTHER PUBLICATIONS

De Palma et al., "Plastic prosthesis versus expandable metal stents for palliation of inoperable esophageal thoracic carcinoma: a controlled prospective study", Gastrointestinal Endoscopy, pp. 478-482, vol. 43, No. 5, 1996.*

ASM International, Materials Park, Ohio, vol. 3: Alloy Phase Diagrams, "Binary Alloy Phase Diagrams", pp. 2•40, 2•80, 2•162, 2•182, 2•207, 2•269, 2•291, and 2•322, Dec. 1992.*

"Eutectoid." Dictionary.com Unabridged. Random House, Inc. Apr. 17, 2014. <Dictionary.com http://dictionary.reference.com/browse/Eutectoid>.*

Murray, Joanne L. "The Co—Ti (Cobalt—Titanium) system." Bulletin of Alloy Phase Diagrams 3.1 (1982): 74-85.*

Murray, Joanne L. "The Ir—Ti (Iridium—Titanium) system." Bulletin of Alloy Phase Diagrams 3.2 (1982): 205-211.*

Murray, Joanne L. "The Pd—Ti (Palladium—titanium) system." Bulletin of Alloy Phase Diagrams 3.3 (1982): 321-329.*

U.S. Appl. No. 09/895,415, filed Jul. 2, 2001.

U.S. Appl. No. 10/232,265, filed Aug. 30, 2002.

U.S. Appl. No. 10/335,604, filed Jan. 2, 2003.

V. Kandarpa, L.R., "Structural and Mechanical Properties of Ti—Ir Alloys," *Proceedings of the Second International Conference on Mechanical Behavior of Materials*, pp. 1737-1740 (1976).

Aaronson et al., "The Bainite and Massive Transformations in Ti-X Eutectoid Systems," *U.S. Department of Commerce National Technical Information Service*, pp. 1-15 (1976).

Eric A. Brandes, Smithells Metals Reference Book, $6^{th}$ Edition, p. 11-140 (Ti—Bi), 1983, Butterworth & Co. London, England.

Ralls, Kenneth M. et al., "Other Three-Phase Reactions in Binary Systems," Introduction to Materials Science and Engineering, John Wiley & Sons (1976). pp. 328-331. 4 pages.

* cited by examiner

MEDICAL DEVICES HAVING ALLOY COMPOSITIONS

CROSS-REFERENCE TO RELATED APPLICATION

This application claims the benefit of the filing date of U.S. Provisional Patent Application Ser. No. 60/844,897, filed on Sep. 15, 2006, the entire contents of which are hereby incorporated by reference.

TECHNICAL FIELD

The invention relates to medical devices including alloy compositions, and the alloy compositions.

BACKGROUND

The body includes various passageways such as arteries, other blood vessels, and other body lumens. These passageways sometimes become occluded or weakened. For example, the passageways can be occluded by a tumor, restricted by plaque, or weakened by an aneurysm. When this occurs, the passageway can be reopened or reinforced, or even replaced, with a medical endoprosthesis. An endoprosthesis is typically a tubular member that is placed in a lumen in the body. Examples of endoprostheses include stents, stent-grafts, and covered stents.

An endoprosthesis can be delivered inside the body by a catheter that supports the endoprosthesis in a compacted or reduced-size form as the endoprosthesis is transported to a desired site. Upon reaching the site, the endoprosthesis is expanded, for example, so that it can contact the walls of the lumen.

To support a passageway open, endoprostheses are made of materials, such as low-carbon, austenitic stainless steel or Nitinol (a nickel-titanium alloy), having appropriate mechanical properties, such as tensile strength and yield strength.

When the endoprosthesis is advanced through the body, its progress can be monitored, e.g., tracked, so that the endoprosthesis can be delivered properly to a target site. After the endoprosthesis is delivered to the target site, the endoprosthesis can be monitored to determine whether it has been placed properly and/or is functioning properly.

Methods of tracking and monitoring a medical device include X-ray fluoroscopy, computed tomography (CT), and magnetic resonance imaging (MRI). MRI is a non-invasive technique that uses a magnetic field and radio waves to image the body. In MRI procedures, the patient is exposed to a magnetic field, which interacts with certain atoms, e.g., hydrogen atoms, in the patient's body. Incident radio waves are then directed at the patient. The incident radio waves interact with atoms in the patient's body, and produce characteristic return radio waves. The return radio waves are detected by a scanner and processed by a computer to generate an image of the body.

SUMMARY

The invention relates to medical devices including alloy compositions, and the compositions.

In one aspect, the invention features a medical device including a eutectoid Ti or Zr alloy having at least two phases and including one or more of Ir, Pt, Cr, Au, Ag, Bi, Mn, Pd, Co, Ni, Cu, and Fe.

In another aspect, the invention features a medical device including a eutectoid alloy having a lamellae microstructure with a width of about 0.1 to about 10 microns.

In another aspect, the invention features a medical device including a composition, the composition includes a mixture, which includes a first phase and a plurality of regions including a second phase. The first phase includes titanium. The second phase includes titanium and a first element. Each region of the plurality of regions has an average width of from approximately 0.1 micrometer to approximately 10 micrometers.

In another aspect, the invention features a medical device including a composition, the composition includes a mixture, which includes a first phase and a plurality of regions including a second phase. The first phase includes zirconium. The second phase includes zirconium and a first element. Each region of the plurality of region has an average width of from approximately 0.1 micrometer to approximately 10 micrometers.

In another aspect, the invention features a method of making a medical device. The method includes providing an alloy of eutectoid composition, and processing the alloy by shaping to form a medical device. After at least one shaping step, the alloy is treated to form a eutectoid alloy.

In another aspect, the invention features a method of making a medical device. The method includes combining and melting a first and second element to form a solid ingot, forming the ingot into a bar, homogenizing and heat treating the bar, forming the bar into a tube, solution annealing the tube, aging the tube to form a composite microstructure, and cutting, cleaning, and polishing the tube into a medical device.

In yet another aspect, the invention features a method of making a medical device. The method includes combining and melting a first and second element to form a solid ingot, forming the ingot into a bar, homogenizing and heat treating the bar, forming the bar into a tube, cutting, cleaning and polishing the tube into the medical device, solution annealing the medical device, and aging the medical device to form a composite microstructure.

Embodiments can include one or more of the following features.

The first phase can consist essentially of titanium or zirconium. In some embodiments, the first phase consists essentially of α-titanium, β-titanium, α-zirconium, or β-zirconium.

The composition can include from approximately 60 percent to approximately 99 percent by weight of the first phase. The composition can include a binary intermetallic alloy.

The composition can have a microstructure including lamellae. In some embodiments, the lamellae have an average width of from approximately 0.1 microns to approximately 10 microns. The lamellae can have an average length of approximately 1 micron to approximately 1000 microns. The lamellae microstructure can have a length to width ratio of about 10:1 to about 10,000:1.

In some embodiments, the second phase includes titanium and a first element, such as Ir, Pt, Cr, Au, Ag, Bi, Mn, Pd, Co, Ni, Cu, or Fe. The first element can have a greater density than titanium. In some embodiments, the second phase consists essentially of titanium and the first element. The second phase can include $Ti_3Ir$, $Ti_3Pt$, $\alpha\text{-}TiCr_2$, $Ti_3Au$, $Ti_2Ag$, $Ti_3Bi$, $\alpha\text{-}TiMn$, $Ti_2Pd$, $Ti_2Co$, $Ti_2Cu$, $TiFe$, or $Ti_2Ni$. The second phase can include from approximately 10 percent to approximately 30 percent by weight Ag or Au (e.g., greater than or equal to approximately ten percent by weight, approximately 15 percent by weight, or approximately 20 percent by weight;

and/or less than or equal to approximately 30 percent by weight, approximately 20 percent by weight, or approximately 15 percent by weight). In some embodiments, the second phase includes approximately 15±2 percent by weight Au, and/or 16±2 percent Ag. The second phase can include from approximately 10 percent to approximately 40 percent by weight Bi (e.g., greater than or equal too approximately 10 percent by weight, approximately 20 percent by weight, approximately 25 percent by weight, approximately 30 percent by weight; and/or less than or equal to approximately 40 percent by weight, approximately 30 percent by weight, approximately 25 percent by weight, or approximately 20 percent by weight). In some embodiments, the second phase includes approximately 29±2 percent by weight Bi. The second phase can include from approximately two percent to approximately 20 percent by weight Co or Ni (e.g., greater than or approximately equal to two percent by weight, approximately five percent by weight, approximately 10 percent by weight, or approximately 15 percent by weight; and/or less than or equal to approximately 20 percent by weight, approximately 15 percent by weight, approximately 10 percent by weight, or approximately five percent by weight). In some embodiments, the second phase includes approximately 8.5±2 percent by weight Co, and/or 6±2 percent by weight Ni. The second phase can include from approximately two percent to approximately 30 percent by weight Cr, Cu, Fe, or Mn (e.g., greater than or equal to approximately two percent by weight, approximately five percent by weight, approximately 10 percent by weight, approximately 15 percent by weight, or approximately 20 percent by weight; and/or less than or equal to approximately 30 percent by weight, approximately 20 percent by weight, approximately 15 percent by weight, approximately 10 percent by weight, or approximately five percent by weight). In some embodiments, the second phase includes approximately 13±2 percent by weight Cr, approximately 7±2 percent by weight Cu, approximately 17±2 percent by weight Fe, and/or approximately 17±2 percent by weight Mn. The second phase can include from approximately five percent to approximately 35 percent by weight Ir (e.g., greater than or equal to approximately five percent by weight, approximately 15 percent by weight, or approximately 25 percent by weight; and/or less than or equal to approximately 35 percent by weight, approximately 25 percent by weight, or approximately 15 percent by weight). In some embodiments, the second phase includes approximately 17±2 percent by weight Ir. The second phase can include from approximately five percent to approximately 30 percent by weight Pd (e.g., greater than or approximately five percent by weight, approximately 15 percent by weight, or approximately 20 percent by weight; and/or less than or equal to approximately 30 percent by weight, approximately 20 percent by weight, or approximately 15 percent by weight). In some embodiments, the second phase includes 19.5±2 percent Pd. The second phase can include from approximately four percent to approximately 30 percent by weight Pt (e.g., greater than or equal to approximately four percent by weight, approximately 10 percent by weight, or approximately 20 percent by weight; and/or less than or equal to approximately 30 percent by weight, approximately 20 percent by weight, or approximately 10 percent by weight). In some embodiments, the second phase includes approximately 12±2 percent by weight Pt.

In some embodiments, the second phase includes zirconium and a first element, such as Ir, Pt, Au, Ag, Ni, or Fe. The first element can have a greater second density than zirconium. In some embodiments, the second phase consists essentially of zirconium and the first element. The second phase can include $Zr_3Ir$, $Zr_5Pt_3$, $Zr_3Au$, $Zr_2Ag$, $Zr_3Fe$, or $Zr_2Ni$. The second phase can include approximately 5±2 percent by weight Au. The second phase can include approximately 2±1.5 percent by weight Ag. The second phase can include approximately 1.5±1 percent by weight Ni. The second phase can include approximately 2.5±2 percent by weight Fe. The second phase can include approximately 6±2 percent by weight Ir. The second phase can include approximately 8.5±2 percent by weight Pt.

The composition can further include a second element, such as Al, Zr, Mo, Sn, Nb, or V. In some embodiments, the composition includes up to approximately five percent by weight Mo, Zr, Sn, or Nb. In some embodiments, the composition includes up to approximately six percent by weight Al. In some embodiments, the composition includes up to approximately 15 percent V.

The composition can have a yield strength greater than or equal to approximately 30 ksi, and/or an elastic modulus greater than or approximately equal to 14 msi.

The medical device can include an endoprosthesis. In some embodiments, the endoprosthesis includes a member capable of maintaining the patency of a bodily vessel, the member can include the composition.

The medical device can include a stent, a stent graft, a guidewire, a needle, a catheter, an intralumenal filter, a staple, a clip, an orthopedic implant, and/or a dental prosthesis.

The method includes a first element. The first element can be Ti or Zr. The method includes a second element. The second element can be Ir, Pt, Cr, Au, Ag, Bi, Mn, or Pd. In some embodiments, the method further includes a third element. The third element can be Al, Zr, Mo, Sn, Nb, or V.

In some embodiments, aging the tube includes aging under a eutectoid temperature to form a eutectoid composite, aging under a eutectoid temperature to form a hypereutectoid composite, and/or aging under a eutectoid temperature to form a hypoeutectoid composite. The composite microstructure can include a lamellar microstructure. In some embodiments, aging the tube includes aging above a eutectoid temperature, at a eutectoid temperature, and/or below a eutectoid temperature.

In some embodiments, shaping includes drilling, drawing, or cutting. In some embodiments, the alloy is provided in the form of a billet or ingot and the shaping includes drilling to form a hollow and the alloy is processed after drilling. In some embodiments, shaping includes drawing to a device diameter and the alloy is processed after drawing.

Embodiments may include one or more of the following advantages. The alloy compositions can have one or more physical and/or mechanical properties, such as radiopacity, MRI compatibility (e.g., low magnetic susceptibility), hardness, strength, stiffness (Young's modulus of elasticity), elongation, and resistance to corrosion, that enhance medical or non-medical applications. For example, the alloy can be formed into a medical device, such as an endoprosthesis. As a result, the endoprosthesis is capable of having a good balance of yield strength and stiffness for a good amount of radial recoil upon expansion to allow good apposition of the endoprosthesis to the vessel wall, and good strength to support a body. The endoprosthesis can also have good radiopacity and MRI compatibility, so that the endoprosthesis can be tracked and monitored. The combination of properties allows the alloys to be formed into a variety of products. The alloys can be relatively cost-effective, for example, compared to alloys having high concentrations of precious metal(s).

The alloy composition can include a metal composite (e.g., a mixture) having a microstructure resolvable only on a microscopic scale (e.g., 100× magnification, 1,000× magnification, 10,000× magnification), which can enhance uniformity of properties of the metal alloy. The alloy composition can have a multi-phase microstructure (e.g., a eutectoid microstructure) that can be reversibly and reproducibly attained. The alloy can be formed into a medical device, which can be relatively easily manufactured. For example, the alloy can be annealed to form a homogeneous solid solution (e.g., for uniform laser cutting and electro-polishing) or can be aged below a specific temperature (e.g., a eutectoid temperature) to afford a multi-phase (e.g., a two-phase, a three-phase) microstructure at any stage in the manufacturing process (e.g., after forming a tube, after cutting a tube, after removal of cut affected areas, and/or after finishing).

The alloy can be relatively easily tailored to afford a desired microstructure. For example, the temperature and/or duration of the heat treatments can be relatively easily changed to afford, for example, an optimal lamellae width, lamellae length, available phases, and phase amounts.

The alloy can be relatively stable. For example, the microstructure (e.g., lamellae, grains, and/or fibers) can be intimately bonded, and delamination or separation can be reduced.

The alloy can also be relatively radiopaque, and radiopacity can be relatively easily incorporated into the alloy with the formation of intermetallic compounds (e.g., compounds formed of Ti and an (or many) element(s) such as Ir, Pt, Cr, Au, Ag, Bi, Mn, Pd, Co, Cu, Fe, and/or Ni).

As used herein, an "alloy" means a substance composed of two or more metals or of a metal and a nonmetal intimately united, for example, by being fused together and dissolving in each other when molten.

As used herein, a "solid solution" is a solid in which one or more elements is homogeneously dispersed in another element at an atomic scale.

As used herein, a "phase" is a region (e.g., a domain) of a material having a substantially homogeneous atomic structure and composition. As an example, a phase can be a cluster of ten or more atoms.

Other aspects, features and advantages will be apparent from the description of the preferred embodiments and from the claims.

DETAILED DESCRIPTION

Figure 1:
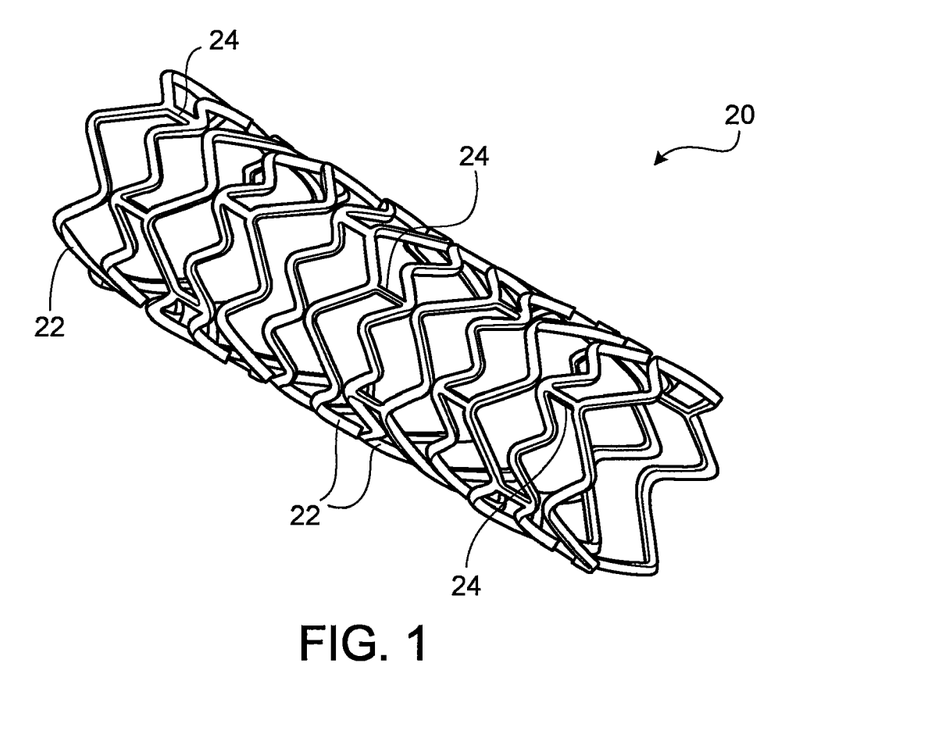
FIG. 1 is a perspective view of an embodiment of an endoprosthesis.

Referring to FIG. 1, an endoprosthesis 20 has the form of a tubular member defined by a plurality of bands 22 and a plurality of connectors 24 that extend between and connect adjacent bands. During use, bands 22 are expanded from an initial, small diameter to a larger diameter to contact endoprosthesis 20 against a wall of a vessel, thereby maintaining the patency of the vessel. Connectors 24 provide endoprosthesis 20 with flexibility and conformability that allow the endoprosthesis to adapt to the contours of the vessel.

In some embodiments, endoprosthesis 20 includes (e.g., is formed of) a metallic alloy that has two (or more) intimately mixed elements. The alloy can be capable of providing endoprosthesis 20 with a good balance of yield strength and stiffness to obtain good radial recoil upon crimping onto the balloon catheter and upon expansion in the vessel. For example, an endoprosthesis can have good securement on the balloon catheter while being tracked along the guidewire to the implantation site and can have good apposition against the vessel wall, strength (for example, to support a body lumen), corrosion resistance, radiopacity, and MRI compatibility.

In particular embodiments, the alloy is a composite structure including ductile domains and stiff domains that provide desirable mechanical properties such that the stent can be delivered in a small diameter form and expanded at a treatment site, can maintain the opening of a lumen wall, and has sufficient flexibility to facilitate delivery through a tortuous body lumen and to avoid excessive stiffness at the treatment site. The domains can be formed by a eutectoid reaction. For example, Ti, which in pure form has a relatively low elastic modulus and density, is utilized in an binary or multi element alloy with elements (X) that form a eutectoid in the Ti rich portion of the phase diagram. The eutectoid composite can form a ductile phase of alpha-Ti and a higher strength phase of Ti—X which provides high strength and stiffness. The eutectoid composite can form microfeatures, such as lamellae that affect mechanical properties and whose characteristics, such as width, length, and concentration can be adjusted during manufacture to select properties of the stent. The microfeatures are intimately bonded, reducing the likelihood of delamination of the composite. The microfeatures can be typically homogeneous throughout the alloy, which enhances uniformity across the stent or between stents. The eutectoid can be formed at multiple stages in the stent manufacturing process, including after drawing or laser cutting by annealing processes, such as aging below the eutectoid temperature, so that the eutectoid is not modified by intermediate processing steps. In addition, the selection of alloy elements can enhance other stent properties, such as radiopacity, for compatibility with fluoroscopic imaging, and magnetic susceptibility, for compatibility with MRI imaging.

Figure 2:
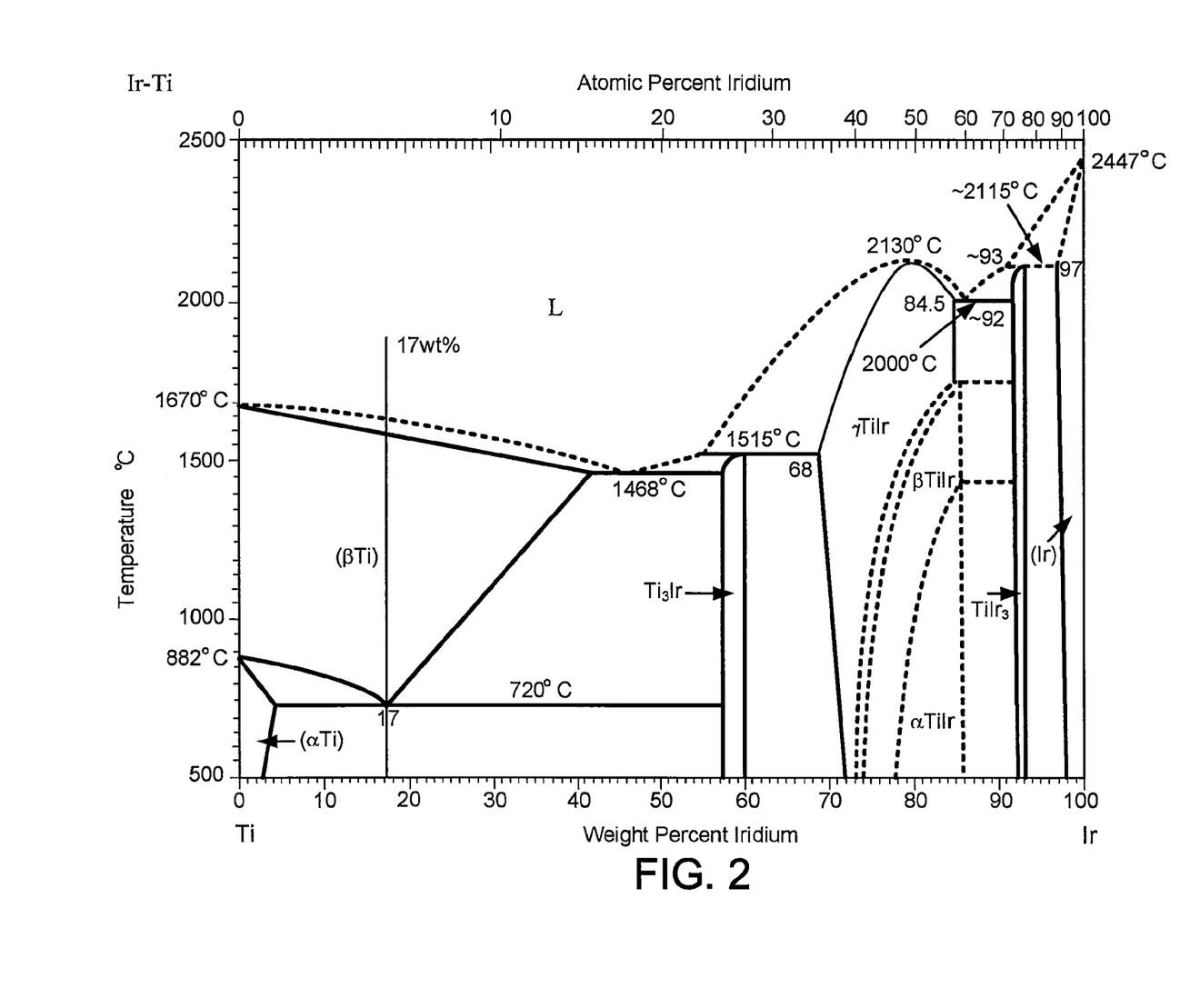
FIG. 2 is a phase diagram.

Referring to FIG. 2, a phase diagram for Ti—Ir binary system is illustrated with the eutectoid composition at 17 wt % marked. The eutectoid composition is the composition of two or more metallic elements, upon cooling, one solid phase transforms isothermally and reversibly into two new solid phases that are intimately mixed. Phase diagrams are provided in Hugh Baker (Ed.). (1992). ASM Handbook, Vol. 3, "Alloy Phase Diagrams". ASM International (Materials Park, Ohio). In particular, phase diagrams for Ti—X binary systems are found at pages 2-38 (Ti—Ag), 2-78 (Ti—Au), 2-150 (Ti—Co), 2-161 (Ti—Cr), 2-180 (Ti—Cu), 2-205 (Ti—Fe), 2-267 (Ti—Ir), 2-290 (Ti—Mn), 2-319 (Ti—Ni), 2-341 (Ti—Pd), 2-348 (Ti—Pt). Further phase diagrams are provided in Eric A. Brandes (Ed.). (1983). Smithells Metals Reference Book (6$^{th}$ Edition, page 11-140 (Ti—Bi)). Butterworth and Co. (London, England).

Figure 3:
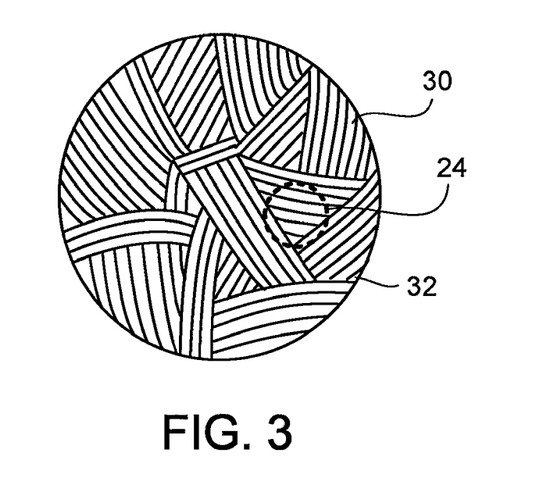
FIG. 3 is a detailed view of an embodiment of an alloy.

Referring to FIG. 3, the metallic alloy includes two (or more) phases that are intimately mixed. The two or more phases can form a composite structure (e.g., a composite microstructure), where the two or more phases can occupy discrete domains within the metallic alloy. The domains can be uniformly, or non-uniformly, dispersed within the metallic alloy. For example, two intimately mixed phases can form a eutectoid structure, where one solid phase 30 can be a relatively ductile matrix phase and the second solid phase 32 can be a relatively strong, stiff, and radiopaque dispersed phase. In the eutectoid structure, the two phases can be reversibly and isothermally transformed between one solid phase and two intimately mixed solid phases. The phases can have various shapes and can be observed using a microscope. For example, a phase can have a lamellar (e.g., layered) appearance, a granular appearance, a globular appearance, a fibrous appearance, and/or a dendritic appearance. As an example, the two phases in the eutectoid structure can have an alternating lamellar microstructure.

Figure 3A:
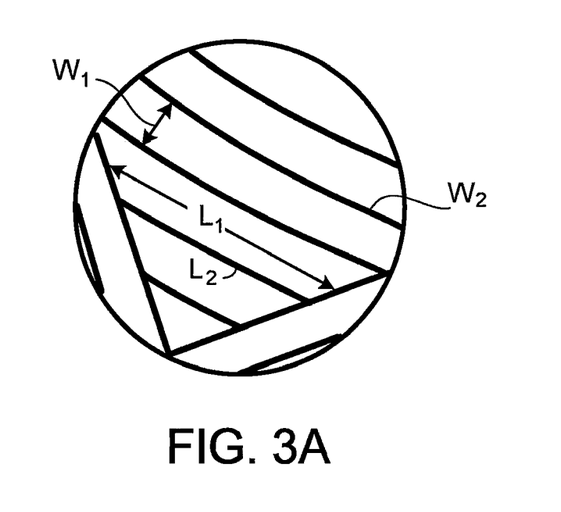
FIG. 3A is an enlarged detailed view of an embodiment of the alloy in FIG. 3.

Referring to FIG. 3A, in some embodiments, a lamellar phase has an average lamella width $W_1$, $W_2$ of from approximately 0.1 µm to approximately 10 µm, and an average length of from approximately 1 µm to approximately 1000 µm. The average lamella width can be greater than or equal to approximately 0.1 µm, approximately 0.2 µm, approximately 0.5 µm, approximately 1 µm, approximately 1.5 µm, approximately 2 µm, approximately 2.5 µm, approximately 3.0 µm, approximately 3.5 µm, approximately 4 µm, approximately 4.5 µm, approximately 5 µm, approximately 5.5 µm, approximately 6.5 µm, approximately 7.5 µm, approximately 8.0 µm; approximately 8.5 µm, or approximately 9.0 µm, and/or less than or equal to approximately 10 µm, approximately 9 µm, approximately 8.5 µm, approximately 8 µm, approximately 7.5 µm, approximately 7 µm, approximately 6.5 µm, approximately 6 µm, approximately 5.5 µm, approximately 5 µm, approximately 4.5 µm, approximately 4 µm, approximately 3.5 µm, approximately 3 µm, approximately 2.5 µm, approximately 2 µm, approximately 1.5 µm, approximately 1 µm, approximately 0.5 µm, or approximately 0.2 µm. The average lamella length $L_1$, $L_2$ can be greater than or equal to approximately 1 µm, approximately 10 µm, approximately 100 µm, approximately 200 µm, approximately 400 µm, approximately 600 µm, or approximately 800 µm; and/or less than or equal to approximately 1000 µm, approximately 800 µm, approximately 600 µm, approximately 400 µm, approximately 200 µm, approximately 100 µm, or approximately 10 µm. The lamellae length and width can be determined by preparing a polished (or polished and etched) metallographic sample cross-section, capturing magnified optical or electron metallographic images of the sample cross-section that include a calibrated micron scale bar or item of known length and then taking distance measurements from the calibrated sample cross-section images. Additional sample preparation guidelines can be found in ASTM E3 "Standard Guide for Preparation of Metallographic Specimens" and ASM Handbook, Volume 9 "Metallography and Microstructures". The average lamellae length and width can be determined by capturing a minimum of five fields-of-view (FOV) from a minimum specimen cross-section area of one square millimeter ($A \geq 1.0$ mm$^2$). The five FOV can be captured at a magnification that is low enough to allow the length of the longest lamella present to be viewed in its entirety, but high enough to clearly discern and measure the width of the narrowest lamella present (e.g. typically between 500× and 3000× magnification). Within each of the five FOV, the length and width of 10 lamellae can be randomly chosen and measured. The average lamellae length can be determined by adding the 50 individual lamellae length measurements from the 5 FOV and dividing by 50. The average lamellae width can be determined by adding the 50 individual lamellae width measurements from the 5 FOV and dividing by 50.

The endoprosthesis can include (e.g., be formed of) an alloy that includes titanium (Ti), which can provide an endoprosthesis that is biocompatible, corrosion resistant, and non-magnetic. The endoprosthesis can also be relatively strong and ductile. In some embodiments, the alloy includes (e.g., is formed of) Ti in a metallic first phase 30. Ti can be in an α-Ti phase that has a hexagonal close-packed crystallographic form and/or in a relatively more ductile β-Ti phase that has a body centered cubic crystallographic form. In some embodiments, the alloy has a Ti concentration from approximately 50 percent by weight to approximately 99 weight percent by weight. The Ti concentration can be greater than or equal to approximately 50 percent by weight, approximately 55 percent by weight, approximately 60 percent by weight, approximately 65 percent by weight, approximately 70 percent by weight, approximately 75 percent by weight, approximately 80 percent by weight, approximately 85 percent by weight, approximately 90 percent by weight, or approximately 95 percent by weight; and/or less than or equal to approximately 99 percent by weight, approximately 98 percent by weight, approximately 97 percent by weight, approximately 96 percent by weight, approximately 95 percent by weight, approximately 90 percent by weight, approximately 85 percent by weight, approximately 80 percent by weight, approximately 75 percent by weight, approximately 70 percent by weight, approximately 65 percent by weight, approximately 60 percent by weight, or approximately 55 percent by weight.

The alloy can also include (e.g., is formed of) one or more metallic second phase 32 having a composition (e.g., a compound) that includes Ti and one or more (e.g., two, three, four, five, six, or more) element(s) such as Ir, Pt, Cr, Au, Ag, Bi, Mn, Pd, Co, Cu, Fe, and/or Ni. In some embodiments, the second phase 32 includes a binary intermetallic compound (e.g., a chemical compound), for example, $TiIr_3$, $Ti_3Pt$, α-$TiCr_2$, $Ti_3Au$, $Ti_2Ag$, $Ti_3Bi$, α-$TiMn$, $Ti_2Pd$, $Ti_2Co$, $Ti_2Cu$, $TiFe$, and/or $Ti_2Ni$. The intermetallic compound can have a greater density than Ti, and can enhance the radiopacity of an endoprosthesis during fluoroscopic and computer tomographic (CT) imaging. An endoprosthesis having an intermetallic compound as part of the alloy can be relatively strong and/or stiff. The endoprosthesis can be non-magnetic and/or compatible for MRI imaging. In some embodiments, the endoprosthesis includes (e.g., is formed of) an alloy that is a mixture of an α-Ti first phase and an intermetallic second phase. In some embodiments, the alloy is a mixture of β-Ti first phase and one or more intermetallic second phases. In certain embodiments, the alloy is mixture of an α-Ti and β-Ti first phase and one or more intermetallic second phases.

In some embodiments, the alloy includes Ir at a concentration from about five percent by weight to about 35 percent by weight. The Ir concentration can be greater than or equal to approximately five percent by weight, approximately eight percent by weight, approximately ten percent by weight, approximately 15 percent by weight, approximately 20 percent by weight, or approximately 25 percent by weight; and/or less than or equal to approximately 35 percent by weight, approximately 30 percent by weight, approximately 25 percent by weight, approximately 20 percent by weight, approximately 15 percent by weight, or approximately ten percent by weight. For example, the alloy can include Ir at a concentration of about 17±2 percent by weight. In some embodiments, Ir is a component of an intermetallic compound such as $Ti_3Ir$, which can have a phase fraction of about 26 percent by weight in the alloy (e.g., the alloy forming the endoprosthesis), a metallic first phase including α-Ti and/or β-Ti can have a phase fraction of about 74 percent by weight in the alloy. As a component in an alloy, Ir can provide a high mass absorption coefficient for enhanced radiopacity in, e.g., fluoroscopy and CT imaging. An alloy including Ir can have low magnetic susceptibility for MRI imaging, high yield strength and/or high Young's modulus, and/or can have noble or substantially inert behavior.

In some embodiments, the alloy includes Pt at a concentration from about four percent by weight to about 30 weight percent by weight. The Pt concentration can be greater than or equal to approximately four percent by weight, approximately ten percent by weight, approximately 15 percent by weight, approximately 20 percent by weight, or approximately 25 percent by weight; and/or less than or equal to approximately 30 percent by weight, approximately 25 percent by weight, approximately 20 percent by weight, approximately 15 percent by weight, or approximately 10 percent by weight. For example, the alloy can include Pt at a concentration of about 12±2 percent by weight. In certain embodiments, Pt is a component of an intermetallic compound such as $Ti_3Pt$, which can have a phase fraction of about 19 percent by weight in the alloy (e.g., the alloy forming the endoprosthesis), a metallic first phase including $\alpha$-Ti and/or $\beta$-Ti can have a phase fraction of about 81 percent by weight in the alloy. As a component in an alloy, platinum can be a good solid solution strengthener, can provide increased strength, can aid in corrosion resistance, can provide low magnetic susceptibility for MRI imaging, and/or can provide a high mass absorption coefficient for enhanced radiopacity.

In some embodiments, the alloy includes Cr at a concentration from about two percent by weight to about 30 percent by weight. The Cr concentration can be greater than or equal to approximately two percent by weight, approximately five percent by weight, approximately ten percent by weight, approximately 15 percent by weight, approximately 20 percent by weight, or approximately 25 percent by weight; and/or less than or equal to approximately 30 percent, approximately 25 percent by weight, approximately 20 percent by weight, approximately 15 percent by weight, approximately ten percent by weight, or approximately five percent by weight. For example, the alloy can include Cr at a concentration of about 13±2 percent by weight. In some embodiments, Cr is a component of an intermetallic compound such as $\alpha$-$TiCr_2$, which can have a phase fraction of about 19 percent by weight in the alloy (e.g., the alloy forming the endoprosthesis), a metallic first phase including $\alpha$-Ti and/or $\beta$-Ti can have a phase fraction of about 81 percent by weight in the endoprosthesis. An alloy containing Cr can have a relatively high stiffness (Young's modulus of elasticity) and enhanced radiopacity. Cr can be a good solid solution strengthener, and can aid in corrosion resistance. Without wishing to be bound by theory, it is believed that chromium can enhance the corrosion resistance of the alloys, e.g., by increasing the pitting resistance of the alloy. For example, in certain alloys, chromium can form a thin oxide layer on the surface of an alloy that enhances the resistance of the alloy to corrosive attack. The degree of corrosion resistance can be a function of the chromium concentration and the concentrations of other elements in the alloy.

In some embodiments, the alloy includes Cu at a concentration from about three percent by weight to about 30 percent by weight. The Cu concentration can be greater than or equal to approximately three percent by weight, approximately five percent by weight, approximately ten percent by weight, approximately 15 percent by weight, approximately 20 percent by weight, or approximately 25 percent by weight; and/or less than or equal to approximately 30 percent by weight, approximately 25 percent by weight, approximately 20 percent by weight, approximately 15 percent by weight, approximately ten percent by weight, or approximately five percent by weight. For example, the alloy can include Cu at a concentration of about 7±2 percent by weight. In some embodiments, Cu is a component of an intermetallic compound such as $Ti_2Cu$ in the metallic second phase, which can have a phase fraction of about 17 percent by weight in the alloy (e.g., the alloy forming the endoprosthesis), a metallic first phase including $\alpha$-Ti and/or $\beta$-Ti can have a phase fraction of about 83 percent by weight in the alloy. An alloy including Cu can have enhanced radiopacity for compatibility with fluoroscopy and CT imaging, and low magnetic susceptibility for compatibility for MRI imaging.

In some embodiments, the alloy includes Fe at a concentration from approximately two percent by weight to approximately 30 percent by weight. The Fe concentration can be greater than or equal to approximately two percent by weight, approximately five percent by weight, approximately ten percent by weight, approximately 15 percent by weight, approximately 20 percent by weight, or approximately 25 percent by weight; and/or less than or equal to approximately 30 percent by weight, approximately 25 percent by weight, approximately 20 percent by weight, approximately 15 percent by weight, approximately ten percent by weight, or approximately five percent by weight. For example, the alloy can include Fe at a concentration of about 17±2 percent by weight. In some embodiments, Fe is a component of an intermetallic compound such as TiFe, which can have a phase fraction of about 31 percent by weight in the alloy (e.g., the alloy forming the endoprosthesis), a metallic first phase including $\alpha$-Ti and/or $\beta$-Ti can have a phase fraction of about 69 percent by weight in the alloy. An alloy including Fe can have enhanced radiopacity.

In some embodiments, the alloy includes Mn at a concentration from approximately two percent by weight to approximately 30 percent by weight. The Mn concentration can be greater than or equal to approximately two percent by weight, approximately five percent by weight, approximately ten percent by weight, approximately 15 percent by weight, approximately 20 percent by weight, or approximately 25 percent by weight; and/or less than or equal to approximately 30 percent by weight, approximately 25 percent by weight, approximately 20 percent by weight, approximately 15 percent by weight, approximately ten percent by weight, or approximately five percent by weight. For example, the alloy can include Mn at a concentration of about 17±2 percent by weight. In some embodiments, Mn is a component of an intermetallic compound such as $\alpha$-TiMn, which can have a phase fraction of about 32 percent by weight in the alloy (e.g., the alloy forming the endoprosthesis), a metallic first phase including $\alpha$-Ti and/or $\beta$-Ti can have a phase fraction of about 68 percent by weight in the alloy. An alloy including Mn can have enhanced radiopacity. In some embodiments, Mn is capable of assisting with phase stabilization, microcleanliness, and hot workability of the alloy to which it is added.

In some embodiments, the alloy includes Au and/or Ag concentration from approximately ten percent by weight to approximately 30 percent by weight. The Au and/or Ag concentrations can be greater than or equal to approximately ten percent by weight, approximately 15 percent by weight, approximately 20 percent by weight, or approximately 25 percent by weight; and/or less than or equal to approximately 30 percent by weight, approximately 25 percent by weight, approximately 20 percent by weight, or approximately 15 percent by weight. For example, the alloy can include Au at a concentration of about 15±2 percent by weight, and/or Ag at a concentration of about 16±2 percent by weight. In some embodiments, Au can be a component of an intermetallic compound such as $Ti_3Au$, which can have a phase fraction of about 18 percent by weight in the alloy (e.g., the alloy forming the endoprosthesis), a metallic first phase including α-Ti and/or β-Ti can have a phase fraction of about 82 percent by weight in the alloy. In some embodiments, Ag is a component of an intermetallic compound such as $Ti_2Ag$, which can have a phase fraction of about 14 percent by weight in the alloy (e.g., the alloy forming the endoprosthesis), a metallic first phase including α-Ti and/or β-Ti can have a phase fraction of about 86 percent by weight in the alloy. An alloy including Au and/or Ag can have enhanced radiopacity and/or low magnetic susceptibility.

In some embodiments, the alloy includes Bi at a concentration from approximately ten percent by weight to approximately 40 percent by weight. The Bi concentration can be greater than or equal to approximately ten percent, approximately 15 percent by weight, approximately 20 percent by weight, approximately 25 percent by weight, approximately 30 percent by weight, or approximately 35 percent by weight; and/or less than or equal to approximately 40 percent by weight, approximately 35 percent by weight, approximately 30 percent by weight, approximately 25 percent by weight, approximately 20 percent by weight, or approximately 15 percent by weight. For example, the alloy can include Bi at a concentration of about 29±2 percent by weight. In some embodiments, Bi is a component of an intermetallic compound such as $Ti_3Bi$, which can have a phase fraction of about 31 percent by weight in the alloy (e.g., the alloy forming the endoprosthesis), a metallic first phase including α-Ti and/or β-Ti can have a phase fraction of about 69 percent by weight in the alloy. An alloy including Bi can have enhanced radiopacity and/or low magnetic susceptibility.

In some embodiments, the alloy includes Pd at a concentration from approximately five percent by weight to approximately 30 percent by weight. The Pd concentration can be greater than or equal to approximately 5 percent by weight, approximately ten percent by weight, approximately 15 percent by weight, approximately 20 percent by weight, or approximately 25 percent by weight; and/or less than or equal to approximately 30 percent by weight, approximately 25 percent by weight, approximately 20 percent by weight, approximately 15 percent by weight, approximately 15 percent by weight, or approximately ten percent by weight. For example, the alloy can include Pd at a concentration of about 19.5±2 percent by weight. In some embodiments, Pd is a component of an intermetallic compound such as $Ti_2Pd$, which can have a phase fraction of about 34 percent by weight in the alloy (e.g., the alloy forming the endoprosthesis), a metallic first phase including α-Ti and/or β-Ti can have a phase fraction of about 66 percent by weight in the alloy. An alloy including Pd can have enhanced radiopacity and/or low magnetic susceptibility.

In some embodiments, the alloy includes Co and/or Ni at a concentration of from approximately two percent by weight to approximately 20 percent by weight. The Co and/or Ni concentrations can be greater than or equal to approximately two percent by weight, approximately five percent by weight, approximately ten percent by weight, or approximately 15 percent by weight; and/or less than or equal to approximately 20 percent by weight, approximately 15 percent by weight, approximately 10 percent by weight, or approximately 5 percent by weight. For example, the alloy can include Co at a concentration of about 8.5±2 percent by weight and/or Ni at a concentration of about 6±2 percent by weight. In some embodiments, Co is a component of an intermetallic compound such as $Ti_2Co$, which can have a phase fraction of about 22 percent by weight in the alloy (e.g., the alloy forming the endoprosthesis), a metallic first phase including α-Ti and/or β-Ti can have a phase fraction of about 78 percent by weight in the alloy. In some embodiments, Ni is a component of an intermetallic compound such as $Ti_2Ni$, which can have a phase fraction of about 15 percent by weight in the alloy (e.g., the alloy forming the endoprosthesis), a metallic first phase including α-Ti and/or β-Ti can have a phase fraction of about 85 percent by weight in the alloy. An alloy including Co and/or Ni can have enhanced radiopacity.

Figure 4:
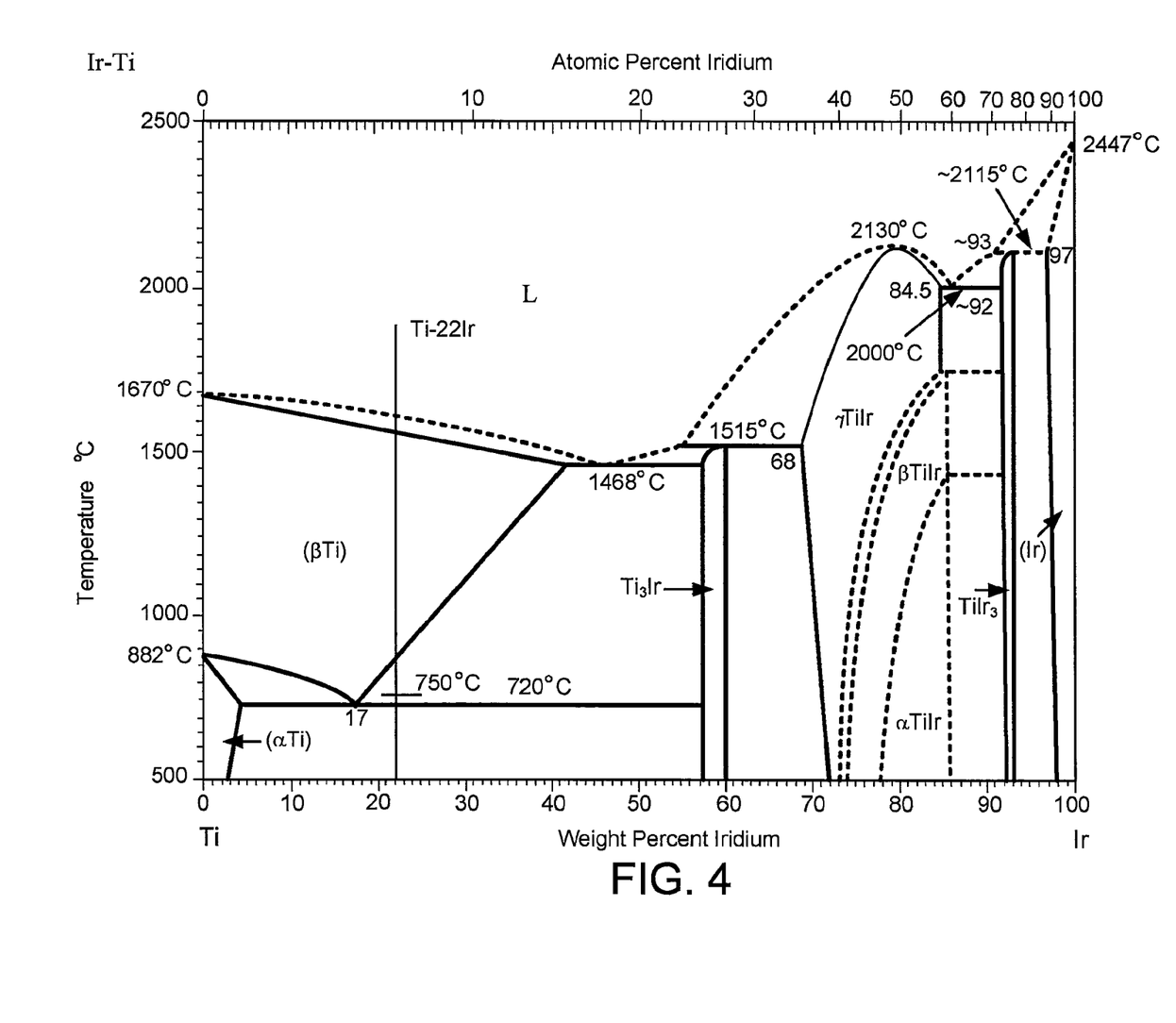
FIG. 4 is a phase diagram.

In some embodiments, an element such as Ir, Pt, Cr, Au, Ag, Bi, Mn, Pd, Co, Cu, Fe, and/or Ni has a concentration greater than a concentration at a eutectoid composition, and the metallic alloy can have a hyper-eutectoid composite microstructure. As an example, referring to FIG. 4., an alloy can include 78 percent by weight Ti and 22 percent by weight Ir. The alloy can be aged at about 750° C. to produce a β-Ti and $Ti_3Ir$ two phase microstructure. A hyper-eutectoid composite microstructure can include phases of various shapes, which can be observed using a microscope. For example, a phase can have a lamellar (e.g., layered) appearance, a granular appearance, a globular appearance, a fibrous appearance, and/or a dendritic appearance.

In some embodiments, an element such as Ir, Pt, Cr, Au, Ag, Bi, Mn, Pd, Co, Cu, Fe, and/or Ni has a concentration less than a concentration at a eutectoid composition, and a metallic alloy can have a hypo-eutectoid composite microstructure. A hypo-eutectoid composite microstructure can include phases of various shapes, which can be observed using a microscope. For example, a phase can have a lamellar (e.g., layered) appearance, a granular appearance, a globular appearance, a fibrous appearance, and/or a dendritic appearance.

In some embodiments, additives such as Al, V, Mo, Sn, Zr, and/or Nb are further added to the alloy composition in various amounts to enhance alloy stability. For example, an alloy can include (e.g., be formed of) Al at a concentration of at most about six percent (e.g., at most about five percent, at most about four percent, at most about three percent, at most about two percent). In some embodiments, Al assists with alloy phase stabilization, and/or increases tensile strength, creep strength, and/or elastic modulus. An alloy can include (e.g., be formed of) V at a concentration of at most about 15 percent (e.g., at most about 12 percent, at most about ten percent, at most about eight percent, at most about six percent, at most about four percent, at most about two percent). In some embodiments, V can stabilize the titanium β-phase. An alloy can include (e.g., be formed of) Mo, Sn, Zr, and/or Nb at a concentration of at most about five percent (e.g., at most about four percent, at most about three percent, at most about two percent). Inclusion of additives can enhance, for example, radiopacity, α-Ti stability, tensile strength, creep strength, elastic modulus, β-Ti stability, corrosion resistance, and/or solid solution strength in the endoprosthesis. For example, Nb can enhance the radiopacity of the alloy and provide the alloy with a low magnetic susceptibility.

In some embodiments, an endoprosthesis includes an alloy having a first phase of β-Ti and a second intermetallic compound.

In some embodiments, the alloy includes (e.g., is formed of) a first phase where Ti can be partially or completely replaced by Zr, and a second phase including a Zr-based intermetallic compound, where the intermetallic compound has a greater density than Zr. The metallic first phase can be an α-Zr phase that has a hexagonal close-packed crystallographic form and/or a relatively more ductile β-Zr phase that has a body centered cubic crystallographic form. The Zr-based intermetallic compound includes, for example, $Zr_3Ir$, $Zr_5Pt_3$, $Zr_3Au$, $Zr_2Ag$, $Zr_3Fe$, and/or $Zr_2Ni$.

In some embodiments, the alloy can include Ir at a concentration of about 6±2 percent by weight. In some embodiments, Ir is a component of an intermetallic compound such as Zr$_3$Ir, which can have a phase fraction of about 16 percent by weight in the alloy (e.g., the alloy forming the endoprosthesis), a metallic first phase including α-Zr and/or β-Zr can have a phase fraction of about 84 percent by weight in the alloy.

In some embodiments, the alloy can include Pt at a concentration of about 8.5±2 percent by weight. In some embodiments, Pt is a component of an intermetallic compound such as Zr$_5$Pt$_3$, which can have a phase fraction of about 16 percent by weight in the alloy (e.g., the alloy forming the endoprosthesis), a metallic first phase including α-Zr and/or β-Zr can have a phase fraction of about 84 percent by weight in the alloy.

In some embodiments, the alloy can include Au at a concentration of about 5±2 percent by weight. In some embodiments, Au is a component of an intermetallic compound such as Zr$_3$Au, which can have a phase fraction of about 13 percent by weight in the alloy (e.g., the alloy forming the endoprosthesis), a metallic first phase including α-Zr and/or β-Zr can have a phase fraction of about 87 percent by weight in the alloy.

In some embodiments, the alloy can include Ag at a concentration of about 2±1.5 percent by weight. In some embodiments, Ag is a component of an intermetallic compound such as Zr$_2$Ag, which can have a phase fraction of about 11 percent by weight in the alloy (e.g., the alloy forming the endoprosthesis), a metallic first phase including α-Zr and/or β-Zr can have a phase fraction of about 89 percent by weight in the alloy.

In some embodiments, the alloy can include Fe at a concentration of about 2.5±2 percent by weight. In some embodiments, Fe is a component of an intermetallic compound such as Zr$_3$Fe, which can have a phase fraction of about 16 percent by weight in the alloy (e.g., the alloy forming the endoprosthesis), a metallic first phase including α-Zr and/or β-Zr can have a phase fraction of about 84 percent by weight in the alloy.

In some embodiments, the alloy can include Ni at a concentration of about 1.5±1 percent by weight. In some embodiments, Ni is a component of an intermetallic compound such as Zr$_2$Ni, which can have a phase fraction of about 5 percent by weight in the alloy (e.g., the alloy forming the endoprosthesis), a metallic first phase including α-Zr and/or β-Zr can have a phase fraction of about 95 percent by weight in the alloy.

In some embodiments, a lamellar phase has an average lamella width of from approximately 0.1 μm to approximately 10 μm, and an average length of from approximately 1 μm to approximately 1000 μm. The average lamella width can be greater than or equal to approximately 0.1 μm, approximately 0.2 μm, approximately 0.5 μm, approximately 1 μm, approximately 1.5 μm, approximately 2 μm, approximately 2.5 μm, approximately 3.0 μm, approximately 3.5 μm, approximately 4 μm, approximately 4.5 μm, approximately 5 μm, approximately 5.5 μm, approximately 6.5 μm, approximately 7.5 μm, approximately 8.0 μm, approximately 8.5 μm, approximately 9.0 μm; and/or less than or equal to approximately 10 μm, approximately 9 μm, approximately 8.5 μm, approximately 8 μm, approximately 7.5 μm, approximately 7 μm, approximately 6.5 μm, approximately 6 μm, approximately 5.5 μm, approximately 5 μm, approximately 4.5 μm, approximately 4 μm, approximately 3.5 μm, approximately 3 μm, approximately 2.5 μm, approximately 2 μm, approximately 1.5 μm, approximately 1 μm, approximately 0.5 μm, or approximately 0.2 μm. The average lamella length can be greater than or equal to approximately 1 μm, approximately 10 μm, approximately 100 μm, approximately 200 μm, approximately 400 μm, approximately 600 μm, or approximately 800 μm; and/or less than or equal to approximately 1000 μm, approximately 800 μm, approximately 600 μm, approximately 400 μm, approximately 200 μm, approximately 100 μm, or approximately 10 μm.

The alloy can further include one (or more) residual amounts of impurities elements. For example, the alloy can include a nitrogen concentration of at most about 0.050 percent by weight (e.g., at most about 0.040 percent by weight, at most about 0.030 percent by weight, at most about 0.015 percent by weight). The alloy can include a carbon concentration of at most about 0.100 percent by weight (e.g., at most about 0.080 percent by weight, at most about 0.060 percent by weight, at most about 0.040 percent by weight). The alloy can include a hydrogen concentration of at most about 0.015 percent by weight (e.g., at most about 0.010 percent by weight, at most about 0.005 percent by weight). The alloy (e.g., a non-iron alloy) can include a maximum iron concentration of at most about 0.5 percent by weight (e.g., at most about 0.4 percent by weight, at most about 0.3 percent by weight, at most about 0.2 percent by weight, at most about 0.1 percent by weight, at most about 0.05 percent by weight, at most about 0.02 percent by weight). The alloy can include an oxygen concentration of at most about 0.2 percent by weight (e.g., at most about 0.1 percent by weight, at most about 0.05 percent by weight, at most about 0.02 percent by weight). Other microalloyed and residual elements are possible, which can be a function of the source of the materials. For example, the alloy can include a yttrium concentration of at most about 0.005 percent by weight (e.g., at most 0.004 percent by weight). The alloy can include a silicon concentration of at most about 0.15 percent by weight (e.g., at most 0.1 percent by weight).

The alloy can have high hardness, high stiffness and/or high strength. In some embodiments, the alloy has a hardness (Rockwell C-Scale Hardness, HRC) from approximately 1.7 HRC to approximately 45 HRC. The hardness can be greater than or equal to approximately 1.7 HRC, approximately 5 HRC, approximately 10 HRC, approximately 15 HRC, approximately 20 HRC, approximately 25 HRC, approximately 30 HRC, approximately 35 HRC, or approximately 40 HRC; and/or less than or equal to approximately 45 HRC, approximately 40 HRC, approximately 35 HRC, approximately 30 HRC, approximately 25 HRC, approximately 20 HRC, approximately 15 HRC, approximately 10 HRC, or approximately 5 HRC. In some embodiments, the alloy can have relatively high stiffness. For example, the alloy can have a Young's modulus of elasticity (E) from approximately 14 msi to approximately 30 msi. The Young's modulus of elasticity can be greater than or equal to approximately 14 msi, approximately 16 msi, approximately 18 msi, approximately 20 msi, approximately 22 msi, approximately 24 msi, approximately 26 msi, or approximately 28 msi; and/or less than or equal to approximately 30 msi, approximately 28 msi, approximately 26 msi, approximately 24 msi, approximately 22 msi, approximately 20 msi, approximately 18 msi, or approximately 16 msi. In some embodiments, the alloy can have an ultimate tensile strength (UTS) from approximately 60 ksi to approximately 220 ksi. The ultimate tensile strength can be greater than or equal to approximately 60 ksi, approximately 100 ksi, approximately 120 ksi, approximately 150 ksi, approximately 180 ksi, or approximately 200 ksi; and/or less than or equal to approximately 220 ksi, approximately 200 ksi, approximately 180 ksi, approximately 150 ksi, approximately 120 ksi, or approximately 100 ksi. In some embodiments, the alloy can have a 0.2 percent offset yield strength (YS) from approximately 30 ksi to approximately 200 ksi. The offset yield strength can be greater than or equal to approximately 30 ksi, approximately 50 ksi, approximately 100 ksi, approximately 150 ksi, or approximately 175 ksi; and/or less than or equal to approximately 200 ksi, approximately 175 ksi, approximately 150 ksi, approximately 100 ksi, or approximately 50 ksi. In some embodiments, the alloy can have a percent elongation (% el) of from approximately 2% el to approximately 30% el. The percent elongation can be greater than or equal to approximately 2% el, approximately 5% el, approximately 10% el, approximately 15% el, approximately 20% el, or approximately 25% el; and/or less than or equal to approximately 30% el, approximately 25% el, approximately 20% el, approximately 15% el, approximately 10% el, or approximately 5% el.

An alloy microstructure (e.g., a eutectoid microstructure) can be observed using a microscope (e.g., optical microscope) at a magnification of from about 100× to 10,000×. The magnification can be at least about 100×, at least about 500×, at least about 1,000×, at least about 2,500×, at least about 5,000×, at least about 7,500×, or at least about 9,000×; and/or at most about 10,000×, at most about 9,000×, at most about 7,500×, at most about 5,000×, at most about 2,500×, at most about 1,000×, or at most about 500×.

Figures 5, 6:
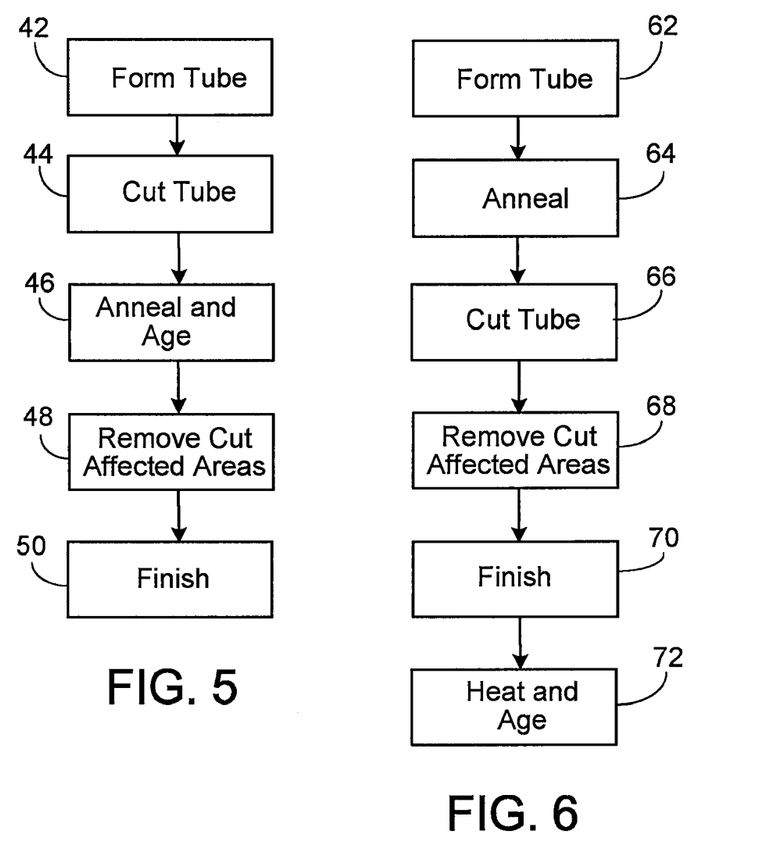
FIG. 5 is a flow chart of an embodiment of a method of making an endoprosthesis.
FIG. 6 is a flow chart of an embodiment of a method of making an endoprosthesis.

Referring to FIG. 5, a method 40 of making endoprosthesis 20 is shown. Method 40 includes forming a tube (step 42) including the alloy that makes up the tubular member of endoprosthesis 20. The tube is subsequently cut to form bands 22 and connectors 24 (step 44) to produce an unfinished endoprosthesis. The unfinished endoprosthesis (e.g., a pre-endoprosthesis) can be annealed and aged at a specific temperature to afford, for example, a desired microstructure (step 46). Areas of the unfinished endoprosthesis affected by the cutting may be subsequently removed (step 48) to form a pre-endoprosthesis. The pre-endoprosthesis can be finished to form endoprosthesis 20 (step 50).

The alloy can be synthesized by intimately combining the components of the alloy. For example, a targeted alloy composition can be formed by melting elemental starting materials (e.g., elemental bits or powders) in the appropriate concentrations under inert conditions to form an ingot. Melting can be performed using consumable-electrode vacuum-melting (e.g., skull melting), vacuum induction melting (VIM), vacuum arc remelting (VAR), electron beam melting (EBM), plasma melting, vacuum or inert gas plasma deposition. Alloying can be performed in the solid state via powdered metallurgy, e.g., by blending elemental powders and hot isostatic pressing at temperatures greater than about 850° C. and less than about 950° C. for 2 to 4 hours at about 15 ksi pressure, and/or cold isostatic pressing at ambient temperature at about 45 to 60 ksi pressure and sintering at temperatures greater than about 1000° C. and less than about 1300° C. for 2 to 3 hours. The alloy can be in the form of an ingot, a compact, or a deposit that is subsequently shaped into a feedstock, such as a hollow tubular member. In some embodiments, the ingot is converted into bar stock via forging, extrusion, and/or rolling operations. In some embodiments, the heat-treated bar is gun-drilled. In some embodiments, the alloy is processed by heat treatment at a temperature from approximately 450° C. to 1100° C. for approximately 15 minutes to 48 hours to homogenize the alloy and/or to yield an alloy with a selected structure and properties.

In some embodiments, the hollow tubular member including the alloy is drawn through a series of dies with progressively smaller circular openings to plastically deform the member to a targeted size and shape (e.g., a tube of step 42). The plastic deformation strain can harden the member (and increases its yield strength) and elongate the grains along the longitudinal axis of the member. The deformed member can be heat treated (e.g., annealed below or above the recrystallization temperature) to transform the elongated grain structure into a partial or fully recrystallized grain structure, e.g., one including equiaxed grains. Small or fine grains can be formed by heating the member close to the recrystallization temperature for a short time. Large or coarse grains can be formed by heating the member at higher temperatures and/or for longer times to promote grain growth.

In some embodiments, the tube from step 42 is solution annealed followed by an aging treatment at a specific temperature (e.g., below a eutectoid temperature, above a eutectoid temperature) to produce, for example, a tube having a two-phase microstructure (e.g., a eutectoid microstructure, a hyper-eutectoid microstructure) of step 44. In some embodiments, the tube from step 42 is directly aged at a specific temperature (e.g., below a eutectoid temperature, above a eutectoid temperature) to produce, for a example, a tube having a two-phase microstructure (e.g., a eutectoid microstructure) of step 44. In some embodiments, the aging treatment can produce a specific alloy microstructure, such as a lamellar microstructure. For example, aging treatments can be tailored to afford a variety of lamellae width, lamellae length, numbers of phases, and phase amount to afford an alloy with desired properties. In some embodiments, aging treatment can occur at a temperature from approximately 450° C. to about 855° C. The temperature can be greater than or equal to approximately 450° C., approximately 500° C., approximately 600° C., approximately 700° C., or approximately 800° C.; and/or less than or equal to approximately 855° C., approximately 800° C., approximately 700° C., approximately 600° C., or approximately 500° C. In some embodiments, aging treatment times is from approximately 15 minutes to approximately 48 hours. The aging time can be greater than or equal to approximately 15 minutes, approximately one hour, approximately five hours, approximately ten hours, approximately 15 hours, approximately 20 hours, approximately 24 hours, approximately 36 hours, or approximately 40 hours; and/or less than or equal to approximately 48 hours, approximately 40 hours, approximately 36 hours, approximately 24 hours, approximately 20 hours, approximately 15 hours, approximately ten hours, approximately five hours, approximately one hour. In some embodiments, the annealing and aging treatment heat-up and cool-down rates can be relatively fast (e.g., 1000° C. per minute) or can be relatively slow (e.g., 1° C. per minute).

Next, bands 22 and connectors 24 of endoprosthesis 20 are formed, as shown, by cutting the tube (step 46). Selected portions of the tube can be removed to form bands 22 and connectors 24 by laser cutting, as described in U.S. Pat. No. 5,780,807, hereby incorporated by reference in its entirety. In certain embodiments, during laser cutting, a liquid carrier, such as a solvent or an oil, is flowed through the lumen of the tube. The carrier can prevent dross formed on one portion of the tube from re-depositing on another portion, and/or reduce formation of recast material on the tube. Other methods of removing portions of the tube can be used, such as mechanical machining (e.g., micro-machining), electrical discharge machining (EDM), and photoetching (e.g., acid photoetching).

In some embodiments, after bands 22 and connectors 24 are formed, areas of the tube affected by the cutting operation above are removed (step 48). For example, laser machining of bands 22 and connectors 24 can leave a surface layer of melted and resolidified material and/or oxidized metal that can adversely affect the mechanical properties and performance of endoprosthesis 20. The affected areas can be removed mechanically (such as by grit blasting or honing) and/or chemically (such as by etching or electropolishing). In some embodiments, the tubular member is near net shape configuration after step 46 is performed. "Near-net size" means that the tube has a relatively thin envelope of material that is removed to provide a finished endoprosthesis. In some embodiments, the tube is formed less than about 25% oversized, e.g., less than about 15%, 10%, or 5% oversized.

The unfinished endoprosthesis is then finished to form endoprosthesis 20 (step 50). The unfinished endoprosthesis can be finished, for example, by electropolishing to a smooth finish. Since the unfinished endoprosthesis can be formed to near-net size, relatively little of the unfinished endoprosthesis need to be removed to finish the endoprosthesis. As a result, further processing (which can damage the endoprosthesis) and costly materials can be reduced. In some embodiments, about 0.0001 inch of the endoprosthesis material is removed by chemical milling and/or electropolishing to yield a endoprosthesis.

Referring now to FIG. 6, in some embodiments, a hollow tubular member of a targeted size and shape is made in an analogous manner 62 as the tube resulting from step 42. The tube can then be stress relieved or solution annealed into a relaxed condition at a temperature from approximately 450° C. to 1100° C. for approximately 15 minutes to 48 hours (step 64). Next, bands 22 and connectors 24 of endoprosthesis 20 are formed in step 66, as shown, by cutting the tube as previously described for step 46. The affected areas can be removed (step 68) to form a pre-endoprosthesis, which can be cleaned and polished in step 70 as previously described for step 50. Finally, the finished pre-endoprosthesis can be loaded into a furnace and aged at a specific temperature in step 72 as previously described for step 44 (e.g., below a eutectoid temperature, above a eutectoid temperature) to produce, for example, an endoprosthesis having a biphasic microstructure (e.g., a eutectoid microstructure, a hypereutectoid microstructure).

Endoprosthesis 20 can be of a desired shape and size (e.g., coronary stents, aortic stents, peripheral vascular stents, gastrointestinal stents, urology stents, and neurology stents). Depending on the application, endoprosthesis 20 can have a diameter of between, for example, 1 mm to 46 mm. In certain embodiments, a coronary stent has an expanded diameter of from about 2 mm to about 6 mm. In some embodiments, a peripheral stent has an expanded diameter of from about 5 mm to about 24 mm. In certain embodiments, a gastrointestinal and/or urology stent has an expanded diameter of from about 6 mm to about 30 mm. In some embodiments, a neurology stent has an expanded diameter of from about 1 mm to about 12 mm. An abdominal aortic aneurysm (AAA) stent and a thoracic aortic aneurysm (TAA) stent can have a diameter from about 20 mm to about 46 mm. Endoprosthesis 20 can be balloon-expandable, or a combination of self-expandable and balloon-expandable (e.g., as described in U.S. Pat. No. 5,366,504).

In use, endoprosthesis 20 can be used, e.g., delivered and expanded, using a catheter delivery system. Catheter systems are described in, for example, Wang U.S. Pat. No. 5,195,969, Hamlin U.S. Pat. No. 5,270,086, and Raeder-Devens, U.S. Pat. No. 6,726,712. Stents and stent delivery are also exemplified by the Radius® or Symbiot® systems, available from Boston Scientific Scimed, Maple Grove, Minn.

While a number of embodiments have been described above, the invention is not so limited.

While endoprosthesis 20 is shown as being formed wholly of the alloy, in other embodiments, the alloy forms one or more selected portions of the medical device. For example, endoprosthesis 20 can include multiple layers in which one or more layers include the alloy, and one or more layers do not include the alloy, e.g., 316L stainless steel. Endoprostheses including multiple layers are described, for example, in published patent application 2004-0044397, and Heath, U.S. Pat. No. 6,287,331.

Endoprosthesis 20 can be a part of a covered stent or a stent-graft. For example, endoprosthesis 20 can include and/or be attached to a biocompatible, non-porous or semi-porous polymer matrix made of polytetrafluoroethylene (PTFE), expanded PTFE, polyethylene, urethane, or polypropylene.

Endoprosthesis 20 can include a releasable therapeutic agent, drug, or a pharmaceutically active compound, such as described in U.S. Pat. No. 5,674,242, U.S. Ser. No. 09/895,415, filed Jul. 2, 2001, and U.S. Ser. No. 10/232,265, filed Aug. 30, 2002. The therapeutic agents, drugs, or pharmaceutically active compounds can include, for example, anti-thrombogenic agents, antioxidants, anti-inflammatory agents, anesthetic agents, anti-coagulants, and antibiotics.

In some embodiments, an endoprosthesis is formed by fabricating a wire including the alloy, and knitting and/or weaving the wire into a tubular member.

The alloys can be used to form other medical devices, such as those that benefit from having high strength to resist overloading and fracture, high corrosion resistance, and/or biocompatibility (e.g., capable of being implanted in a body for long periods (such as greater than ten years)), particularly medical implants and devices that will be used with fluoroscopy and/or MRI during a medical procedure or when patients will be subjected to follow-up MRI imagery. For example, the alloys can be used to manufacture other endoprostheses. The alloys can be used in filters such as removable thrombus filters described in Kim et al., U.S. Pat. No. 6,146,404, which is hereby incorporated by reference; in intravascular filters such as those described in Daniel et al., U.S. Pat. No. 6,171,327, which is hereby incorporated by reference; and vena cava filters such as those described in Soon et al., U.S. Pat. No. 6,342,062, which is hereby incorporated by reference.

The alloys can be used to form a guidewire (such as a Meier Steerable Guide Wire (for AAA stent procedure)), an ASAP Automated Biopsy System (e.g., for a stylet and/or a cannula, as described in U.S. Pat. Nos. 4,958,625, 5,368,045, and 5,090,419), or a hypotube of a catheter (e.g., a balloon catheter).

The alloys can also be used to manufacture cutting elements, such as those carried by a medical balloon catheter described in U.S. Ser. No. 10/335,604, filed Jan. 2, 2003, and U.S. Pat. No. 5,209,799, and U.S. Pat. No. 5,336,234. The hardness and strength of the alloys can reduce edge rounding (which can decrease sharpness) and deformation of the product shape. Also, in some cases, the relatively high corrosion resistance of the alloys allows the instruments to be exposed to repeated steam autoclave sterilization cycles. As a result, the instruments can be reused more, and the cost of replacement is reduced.

Still other examples of medical devices include, needles, catheters, staples, wires used for wound closure, clips, orthopedic devices (such as hip stems and knee trays), and dental prostheses.

The following example is illustrative and not intended to be limiting.

Example 1

Figure 7:
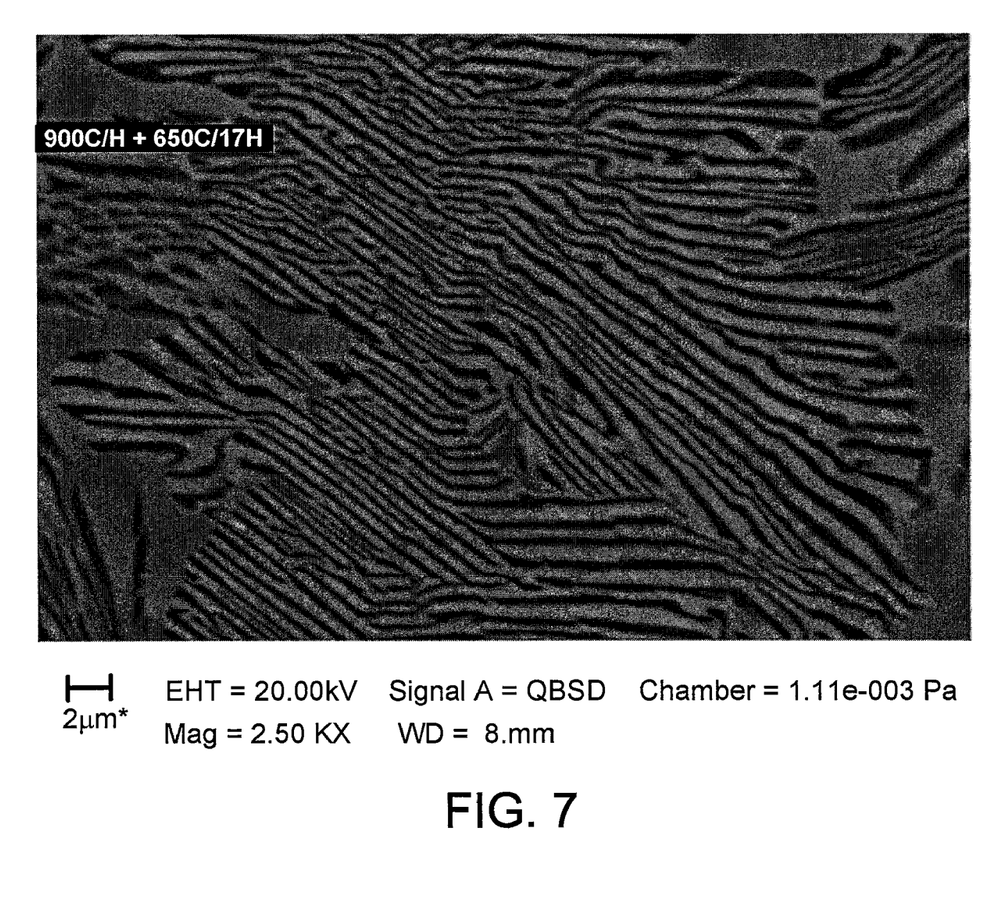
FIG. 7 is a microscopic view of an alloy.

An ingot having 17 percent by weight Ir and 83 percent by weight Ti is produced using an arc melter at a temperature of 3,000° C. and at a vacuum pressure of 30 in Hg. The ingot is homogenized and machined into a 0.2" thick rolling blank. The rolling blank is hot and cold rolled into a strip of less than 0.020 inch thickness. Next, the strip metal is machined into dog-bone tensile specimens, which is solution heat-treated at 900° C. for 1 hour followed by an age treatment at 650° C. for 17 hours. Referring to FIG. 7, a backscatter electron SEM image of an as-polished metallographic cross-section at 2,500× magnification, 20.00 kV accelerating voltage, 8 mm working distance, and 1.11E-003 Pa chamber vacuum pressure shows a lamellae microstructure of the resulting eutectoid alloy. An elastic modulus of 18.6 Msi is obtained.

The above ingot can be formed into an endoprosthesis as follows. The ingot can be drawn into a tube. Endoprosthesis strut patterns can be laser machined into the drawn tubing. Post-laser dross removal and electropolishing can be performed to produce finished endoprosthesis dimensions. The endoprostheses can be crimped onto balloon catheters.

All publications, references, applications, and patents referred to herein are incorporated by reference in their entirety.

Other embodiments are within the claims.

What is claimed is:
1. A medical device, comprising:
a composition comprising a mixture comprising
   a first phase comprising titanium, and
   a plurality of regions comprising a second phase different from the first phase, the second phase comprising titanium and a first element, each region of the plurality of regions having an average width of from approximately 0.1 $\mu$m to approximately 10 $\mu$m,
wherein the composition comprises from approximately 10 percent to approximately 40 percent by weight Bi.

* * * * *